(12) United States Patent
Singh

(10) Patent No.: US 10,939,920 B2
(45) Date of Patent: Mar. 9, 2021

(54) HEMODIALYSIS VEIN PREPARATION METHOD

(71) Applicant: Tej M. Singh, Los Altos, CA (US)

(72) Inventor: Tej M. Singh, Los Altos, CA (US)

(*) Notice: Subject to any disclaimer, the term of this patent is extended or adjusted under 35 U.S.C. 154(b) by 241 days.

(21) Appl. No.: 15/866,748

(22) Filed: Jan. 10, 2018

(65) Prior Publication Data
US 2019/0209182 A1 Jul. 11, 2019

(51) Int. Cl.
*A61B 17/135* (2006.01)
*A61B 17/132* (2006.01)

(52) U.S. Cl.
CPC ........ *A61B 17/135* (2013.01); *A61B 17/1325* (2013.01); *A61B 17/1355* (2013.01)

(58) Field of Classification Search
CPC ..... A61B 17/132–1355; A61M 1/3655; A61H 9/0078–0092
See application file for complete search history.

(56) References Cited

U.S. PATENT DOCUMENTS

| | | | |
|---|---|---|---|
| 6,905,456 B1 * | 6/2005 | Brunner | A61H 9/0078 600/16 |
| 2009/0234261 A1 * | 9/2009 | Singh | A61B 17/1325 601/152 |
| 2011/0240043 A1 * | 10/2011 | Redington | A61B 17/1327 128/898 |

OTHER PUBLICATIONS

Rus, R. R., Ponikvar, R., Kenda, R. B., & Buturović-Ponikvar, J. (2005). Effect of intermittent compression of upper arm veins on forearm vessels in patients with end-stage renal disease. Hemodialysis International, 9(3), 275-280. (Year: 2005).*

* cited by examiner

*Primary Examiner* — Thomas McEvoy
(74) *Attorney, Agent, or Firm* — Baker Donelson Bearman Caldwell & Berkowitz, PC

(57) ABSTRACT

A method for applying focused pressure to a target vessel to dilate the target vessel for hemodialysis. The target vessel is treated with pressure multiple times a day prior to a fistula surgical procedure to increase the vein size. The target vessel is also treated with pressure multiple times a day after the fistula surgical procedure to increase or maintain the vein size.

45 Claims, 10 Drawing Sheets

FIG. 9C1

| Gender (in %) and Age | DM (in %) | HTN (in %) |
|---|---|---|
| Female- 20.34<br>Mean Age- 53.50<br>Standard Deviation- 14.90 | No- 45.76<br><br>Yes- 54.24 | No- 10.17<br><br>Yes- 89.83 |
| n=12<br><br>Male- 79.66<br>Mean Age- 51.53<br>Standard Deviation- 15.39<br>n=47 | | |

FIG. 12

| Variable | FISTULA | N | Mean | SE Mean | StDev | Q1 | Median | Q3 |
|---|---|---|---|---|---|---|---|---|
| Percent Vein 5cm | BCF | 24 | 36.68 | 8.08 | 39.57 | 9.32 | 20.00 | 43.53 |
|  | RCF | 19 | 85.0 | 11.2 | 48.9 | 45.5 | 85.7 | 100.0 |
|  |  |  |  |  |  |  |  |  |
| Percent Vein 10cm | BCF | 24 | 39.32 | 7.24 | 35.47 | 8.70 | 36.40 | 51.50 |
|  | RCF | 19 | 93.5 | 10.2 | 44.6 | 58.3 | 78.3 | 142.9 |
|  |  |  |  |  |  |  |  |  |
| Percent Vein 15cm | BCF | 24 | 32.46 | 8.51 | 41.67 | 5.44 | 15.69 | 55.98 |
|  | RCF | 19 | 77.9 | 13.0 | 56.9 | 33.3 | 66.7 | 110.0 |

| Variable | Class | N | Mean | SE Mean | St. Dev. | Q1 | Median | Q3 |
|---|---|---|---|---|---|---|---|---|
| Percent Vein 5 cm | 1 | 19 | 85.0 | 11.2 | 48.9 | 45.5 | 85.7 | 100.0 |
| | 2 | 16 | 25.08 | 6.12 | 24.50 | 8.34 | 23.76 | 36.26 |
| | 3 | 24 | 36.68 | 8.08 | 39.57 | 9.32 | 20.00 | 43.53 |
| Percent Vein 10 cm | 1 | 19 | 93.5 | 10.2 | 44.6 | 58.3 | 78.3 | 142.9 |
| | 2 | 16 | 42.07 | 6.39 | 25.58 | 24.07 | 34.48 | 47.11 |
| | 3 | 24 | 39.32 | 7.24 | 35.47 | 8.70 | 36.40 | 51.50 |
| | | | | | | | | |
| Percent Vein 15 cm | 1 | 19 | 77.9 | 13.0 | 56.9 | 33.3 | 66.7 | 110.0 |
| | 2 | 16 | 32.441.526 | 9.76 | 39.05 | 25.95 | 32.96 | 44.81 |
| | 3 | 24 | 32.46 | 8.51 | 41.67 | 5.44 | 15.69 | 55.98 |

FIG. 16

HEMODIALYSIS VEIN PREPARATION METHOD

TECHNICAL FIELD

The application relates to end stage renal disease (ESRD) and more particularly to vessel preparation for hemodialysis.

BACKGROUND OF INVENTION

Many patients in the world suffer from renal failure from multiple underlying conditions including hypertension, genitourinary tract infections, and diabetes, a condition that affects about 20 million people in the United States alone.

Unfortunately, many of these renal failure patients result in progression to ESRD, which requires dialysis where the blood is filtered and when possible eventually a renal transplant. Dialysis options include temporary central catheter treatment, peritoneal dialysis and hemodialysis via fistulae or grafts placed in the arms connecting an artery and vein. The vein is accessed to allow blood to flow from the patient's vein to a dialysis machine, which has a filter that removes waste, surplus fluids, and balances electrolytes. The filtered blood is then returned to the patient's vein downstream from the arterial access site. Many patients and healthcare providers prefer hemodialysis via arms sites as the best hemodialysis option.

If the patient elects hemodialysis as a treatment option for the end stage renal disease, the following procedure is typical. The patient's arm veins are evaluated clinically and measured with duplex ultrasound to find a vein that is 3 mm or larger. A 3 mm vein is a suitable candidate for surgical connection to an artery. The patient's arm arteries are palpated for a pulse to find a target artery to which the vein is to be connected. The physician connects the target artery and vein either at the wrist or elbow depending on the best vein and its location. In this manner, the physician forms a fistula between the two vessels. In the example where the connection is made at the wrist, the fistula can be made between the radial artery and the cephalic vein at the wrist (brescia fistula). The patient is sent home with instructions to exercise his/her hand and arm during the day to increase blood flow in the artery and vein with the hope that this exercise will increase the vein size by the increased flow. One often used exercise technique involves squeezing a device such as a ball with the hope that the vein will enlarge. The patient is observed for about six to eight weeks to monitor if enlargement of the vein has occurred keeping in mind that at least a 6 mm diameter vein would provide for better quality dialysis as compared to a smaller vein diameter. If after weeks of such exercise, the vein does not enlarge or thrombose, alternative treatment options are discussed. Such alternative treatment options include another fistula placement in another location, fistula salvage by endovascular means, synthetic graft placement, or catheter placement.

Many studies have concluded that arm veins connected to arteries provide the most dependable, durable vascular access option for hemodialysis. After this procedure connecting the arm vein and artery, patients are told to wait and watch if their vein becomes large enough to be used for dialysis. It is hard to predict which veins will enlarge to the appropriate size for dialysis use. Unfortunately, many arm veins fail to dilate and enlarge enough after subjecting them to arterial flow to allow for dialysis to occur. Some patients are told that their veins are too small and others are given no justification. This results in more surgery and possible graft placement or prolonged catheter usage at higher costs to society. Each eventual procedure also has increased risks to the patient as dialysis is delayed.

In some cases where the vein is considered sufficiently large for hemodialysis, but below the 10 mm diameter target, it can be more susceptible to function loss in a relatively short period of time during the hemodialysis treatment. Fistulae last longer if the vessel used for dialysis is properly dilated to the target diameter of about 10 mm. The vein being treated undergoes significant trauma as a patient typically undergoes about three hemodialysis sessions per week. Eventually the fistula (vein) to which the artery is connected fails in that it does not stay dilated or functional. This failure can happen more quickly when the vein fails to dilate to the optimum diameter before hemodialysis. Once the vein fails, another vein and artery must be connected to provide another vein for hemodialysis. This process requires surgery and is uncomfortable and there are a limited number of veins that are suitable for dialysis.

Extensive research has shown that intermittent compression, external heat application, and topical agents like nitric oxide help dilate superficial veins. Typically, when a dialysis technician initiates dialysis treatment where a needle is place in the target vein, the technician will apply intermittent pressure on the patient's arm with their fingers to dilate the vein prior to needle placement.

Accordingly, there is a need in the art to provide improved vein dilation methods to sufficiently and/or effectively dilate a vein for hemodialysis or maintain vein dilation for a longer period, while a patient is undergoing hemodialysis treatment. It is to the provision of such therefore that the present invention is primarily directed.

SUMMARY OF THE INVENTION

In a preferred form of the invention, a method for dilating a target vein of a patient being treated for hemodialysis comprises securing a device to a limb of a patient being treated for hemodialysis, the limb being where the target vein, which is suitable for hemodialysis, resides and with the device applying an effective amount of pressure intermittently to a section of the target vein and for an effective amount of time to dilate the vein to a size suitable to provide access for hemodialysis.

In another embodiment according to the invention, a method for dilating a vein of a patient being treated for hemodialysis comprises applying intermittent pressure to a section of a target vein, which is to be accessed for hemodialysis, with a device that is secured to a limb of the patient and includes a compression member that exerts intermittent pressure on a substantially straight external surface portion of the patient's limb to which it is secured so as to dilate the target vein, which is suitable for hemodialysis and is beneath the external surface portion; wherein the compression member has a width of 1-2 cm and does not encircle the patient's limb when secured thereto.

A method for dilating a fistula portion of target vein of a patient being treated for hemodialysis comprising the steps of determining the size of the fistula portion of the target vein, and applying an intermittent pressure to the target vein downstream of the fistula after the surgical formation of the fistula but prior to hemodialysis, the intermittent pressure being applied for a treatment period multiple times a day until the fistula achieves a diameter size of at least 3.5 mm.

A method for dilating a fistula portion of target vein of a patient being treated for hemodialysis comprising the steps of determining the size of a target vein for a fistula portion in the target vein, and applying an intermittent pressure to the target vein downstream of the fistula site prior to the surgical formation of the fistula but prior to hemodialysis, the intermittent pressure being applied for a treatment period multiple times a day until the target vein achieves a diameter size of at least 3.5 mm.

BRIEF DESCRIPTION OF DRAWINGS

FIG. 9C1 illustrates a variation of the embodiment of FIG. 9C.

FIG. 12 is a table showing patient demographics in a case study.

FIG. 16 is a table showing percent increase at one month for the case study of FIG. 12.

DETAILED DESCRIPTION

The following description will be made with reference to the drawings where when referring to the various figures, it should be understood that like numerals or characters indicate like elements. Further, before the present invention is described, it is to be understood that this invention is not intended to be limited to particular embodiments or examples described, as such may, of course, vary.

According to one embodiment of the invention, focused intermittent pressure is applied to a target vein that is to be used for hemodialysis. The pressure is applied along a narrow band of a patient's limb. The pressure can be applied along a narrow band of a patient's limb in a manner in which the pressure is focused on the target vein to dilate the target vein. To assist with applying pressure over a long period of time, any of the illustrated apparatus described herein can be secured to the patient's limb. The illustrated apparatus generally include a compression member, which can be a single inflatable cell or expandable member, multiple inflatable cells or expandable members, or a member that is tracked or rolled over a narrow band of the patient's limb. One example of such a tracked or rolled member is a roller member that is rotatably mounted to the support feature of the device that has been secured to the patient's limb. The compression member, which can be constructed to extend in a direction or move in a direction, extends or moves in a substantially straight direction along an axial direction of the patient's limb or along a length of the patient's limb without encircling the patient's limb and exerts pressure on a narrow, substantially straight external surface portion of the patient's limb so as to dilate the target vein (e.g., the cephalic vein) thereunder according to one configuration of the invention.

The illustrated inflation apparatus described herein are portable and allow the patient to be ambulatory during treatment. Accordingly, the treatment can be carried out completely outside the hospital or hemodialysis clinic or it can be carried out both outside and inside these facilities. As will be apparent from the following description, the patient might wear the apparatus in the hospital to maintain vein dilation up to the time of when the surgeon creates the fistula or in the clinic to maintain vein dilation up to the time of hemodialysis.

Figure 1:
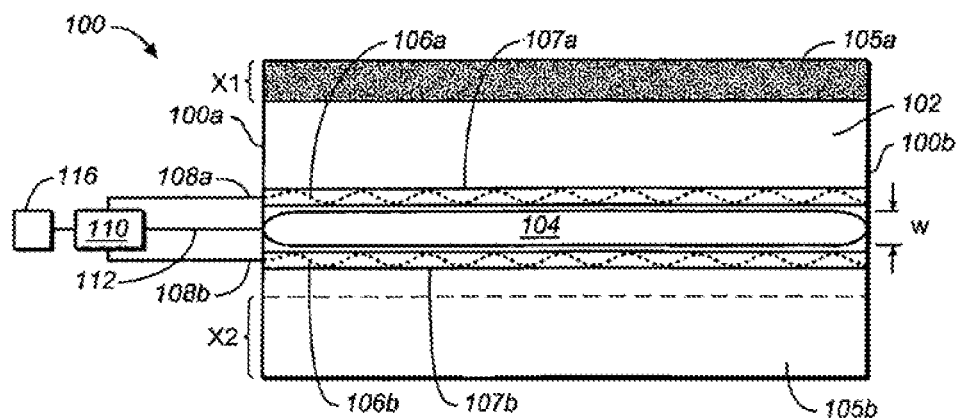
FIG. 1 is a top view of one embodiment of vein dilation apparatus according to the invention.
Figure 2:
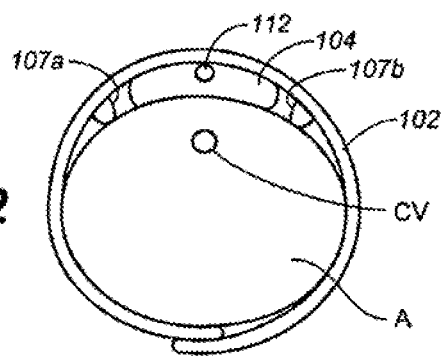
FIG. 2 is an end view of the vein dilation apparatus of FIG. 1 wrapped around a patient's arm.

Referring to FIGS. 1 and 2, one embodiment according to the invention is diagrammatically shown and generally designated with reference numeral 100. Apparatus or device 100 comprises a flexible sheet 102 and compression member 104. Flexible sheet 102 can be fabric or any other suitable material and is adapted to be placed around an arm or leg of a patient to form a sleeve. Compression member 104 in one embodiment comprises an expandable or inflatable member such as a balloon secured to flexible sheet 102. Expandable compression member 104 can be made from any suitable resilient sheet material that will sustain inflation of a fluid medium such as air and in one example can be made from nylon. In another embodiment, compression member 104 can be integrally formed with flexible sheet 102.

In the embodiment shown in FIGS. 1 and 2, compression member 104 is arranged on and secured to the inner surface of the sleeve to provide focused pressure to a target vein to be enlarged. FIG. 2 illustrates one example where apparatus 100 is wrapped around arm "A" with compression member 104 aligned over cephalic vein "CV" to provide focused pressure to the cephalic vein. Typically, element 104 will have a width "W" from 1 cm to and including 2 cm and more typically a width of 1.5 cm. This provides a low profile device suitable for long periods of use where the patient can wear the device, while maintaining normal activity. The relatively narrow width also focuses the pressure on the target zone or vein as compared to a wider inflation member or cylindrical inflation member.

Apparatus 100 has a proximal end 100a, which, for example, can be placed near the patient's elbow, and a distal end 100b, which then would be placed near the patient's wrist when the device is placed on a patient's forearm. In the illustrative embodiment, sheet 102 includes hook and loop fasteners, which can be Velcro® brand hook and loop fasteners. A band 105a of hook fasteners is provided along one side margin of sheet 102 and a band of loops along an opposite side margin 105b on the reverse side of sheet 102 (and thus hidden from view) to enable one to secure the side margins together when the sheet is wrapped to form a sleeve around a patient's limb during use. Although one hook and loop fastener configuration is shown, other configurations can be used as well as other securing mechanisms to secure portions of the sheet together when the sheet is wrapped around a patient's limb and provide the desired fit with the patient's limb for the compression member to transmit the desired pressure to the patient.

An inlet or opening is formed in compression member 104 to fluidly couple compression member 104 to a pressure source that delivers pressurized fluid such as air. The pressure source can be a compressor or pump (e.g., an air pump), which can be configured as a portable device as is known in the art. In one example, it can be a miniature device, which can be secured to the dilation apparatus or the patient with any suitable means such as a strap having hook and loop fastening portions as described above. The control unit or both the control unit and power source (described below) also can be configured to be secured to the dilation apparatus and/or the patient's limb to be carried thereby. Further, the pressure source and the control unit, which can house the pressure source, can be releasably coupled to portable apparatus 100 and the power source releasably coupled to the pressure source and/or control unit. In the embodiment illustrated in FIGS. 1 and 2, tube 112, diagramatically represented with a line, provides a conduit between the inlet port or opening in compression member 104 and the pressure source, which is housed in control unit 110. Control unit 110 is coupled to power source 116, which can be a rechargeable battery or other suitable means for providing power to control unit 110. Control unit 110 controls activation of the pressure source, which can be preset to deliver the desired pressure. Alternatively, control unit 110 can control activation of the pressure source and pressure output from the pressure source (e.g., pump speed) to control delivery of pressurized fluid to compression member 104 at the desired pressure. In another alternative, control unit 110 can control activation of the pressure source and one or more fluid control devices such as valves, which can be operatively coupled to conduit 112 and control unit 110 in a manner such that control unit 110 controls delivery of pressurized fluid to compression member 104. In one example, control unit 110 has a timing circuit and controls pressure delivery from the pressure source to provide intermittent pressure or to intermittently provide a target or peak pressure in inflatable compression member 104 based on the timing circuit. For example, the timing circuit can provide a pressurization cycle where the pressure source delivers the desired pressure (e.g., sufficient pressure to inflate compression member 104 so that it applies sufficient pressure to the patient's limb to occlude blood flow in the target vessel) for a predetermined period of time followed by a predetermined period of time of no pressure delivery or deflation, and this repeated for a preset period of time. The desired pressure applied to the patient's limb can be from about 6 mmHg to about 25 mmHg. Depending on the patient, more pressure can be used if required for vessel occlusion or less pressure may be suitable. An on-off switch can be provided and operatively coupled to control unit 110 (e.g., between the control unit and the power source) to provide a means to start or stop the treatment period. In one arrangement, a solenoid valve can be placed in conduit 112 and operatively coupled to control unit 110 so that control unit 110 controls flow of pressurized fluid to compression member 104 through the solenoid valve based on the timing circuit.

In one variation, sheet 102 can be provided with heating elements 106a and 106b that are positioned along the side of the compression member 104 to enhance dilation of the target vessel. However, it should be understood that these heating elements are optional and are not required. Each heating element can be a conventional heating wire that is sandwiched between sheet 102 and another piece or layer of fabric 107a and 107b, respectively. Leads 108a,b connect heating elements to control unit 110, which delivers the desired power to heating elements 106a,b. Although one heating element configuration is shown, any conventional heating element arrangement can be used. In one variation, temperature sensors can be secured to the heating regions where the heating elements reside in any manner known to one of skill in the art and coupled to control unit 110, which can control power output to the heating elements in response to the sensed temperature to maintain the temperature in these regions to be from about 98 to about 150 degrees Fahrenheit.

In another variation a topical dilating agent (e.g., nitric oxide) is applied to the patient's skin in the region of the target vein before securing the dilation device to the patient with the compression member aligned with the target vessel. The topical agent also can enhance vessel dilation.

Figure 3:
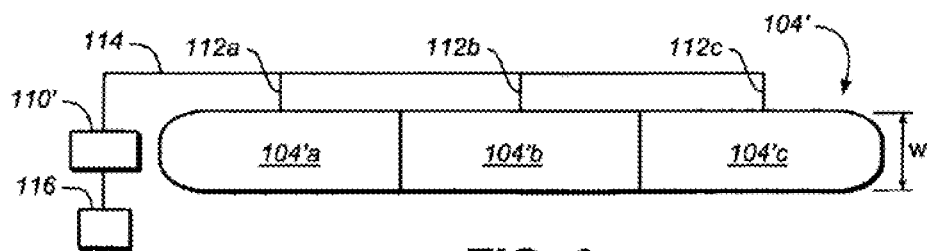
FIG. 3 illustrates a variation of the apparatus of FIG. 1 and diagrammatically illustrates a control circuit for controlling inflatable member inflation.

Referring to FIG. 3, another compression member for use in apparatus 100 is shown. The dilation apparatus embodiment incorporating the compression member of FIG. 3 into the apparatus of FIG. 1 is the same as the embodiment of FIG. 1, with the exception that the compression member configuration differs and the control unit and pressurization conduits modified to accommodate the multi-cell compression member of FIG. 3. In this embodiment, the compression member, which is designated with reference numeral 104', includes a plurality of separate expandable or inflatable compartments or cells (e.g., compartments or cells 104'a, 104'b, and 104'c) that can be inflated and/or deflated according to a desired sequence. For example, they can be inflated serially in a manner that provides a moving compression wave in one direction (e.g., from cell 104'a to cell 104'c or from cell 104'c to cell 104'a) and that cycle repeated for a desired period of time. Compression cells 104'a, 104'b, and 104'c are fluidly coupled to manifold 114 through conduits 112a, 112b, 112c and manifold 114 is fluidly coupled to a pressure source in control unit 110' so that control unit 110' can selectively provide pressure (e.g., pneumatic pressure) to the compression cells according to a predetermined sequence. Any suitable known pressure source such as described above and control mechanism can be used to control fluid delivery to cells 104'a, 104'b, and 104'c and sequentially pressurize the cells according to the desired sequence. Control unit 110' can include a timing circuit to control when fluid under pressure is to be delivered to the cells as described above and to control the cell inflation sequence. Further, a plurality of solenoid valves, which are well known mechanisms for controlling fluid flow, can be operatively coupled to the control unit 110' and conduits 112a,b,c, and control unit 110' provided with a timing circuit so that control unit 110' can control independent pressurization and venting of each compression member cell. Various solenoid valve configurations, which can be used, are disclosed, for example, in U.S. Pat. No. 6,852,089 to Kloecker et al and entitled Compression Garment for Selective Application for Treatment of Lymphedema and Related Illnesses Manifested at Various Locations of the Body, the disclosure of which is incorporated herein by reference. Cell 104'a can be inflated while the other cells are deflated, then cell 104'b inflated while cell 104'a deflated, and then cell 104'c inflated while cell 104'b deflated and that cycle repeated for the treatment period. Alternatively, a single cycle can correspond to successively inflating the cells in one direction until they are all inflated and then deflating all of the cells as described in U.S. Pat. No. 6,010,471 to Ben-Noon and entitled Body Treatment Apparatus, the disclosure of which is hereby incorporated herein by reference.

It also should be understood that although three expandable compartments or cells are shown in the illustrative embodiment, more or fewer compartments or cells can be used.

When pressurized, the pressure in any one of the expandable elements or cells described above provides the desired pressure on the patient's limb as described above (e.g., sufficient pressure is applied to the patient's limb to occlude blood flow in the target vessel) beneath the respective cell. The control unit can be set to provide this pressure.

Compression member 104' has the same width as compression member 104. As described above, a relatively narrow width focuses the pressure of the compression member on the target vein as compared to a wider inflation member or a cylindrical inflation member.

Figure 4:
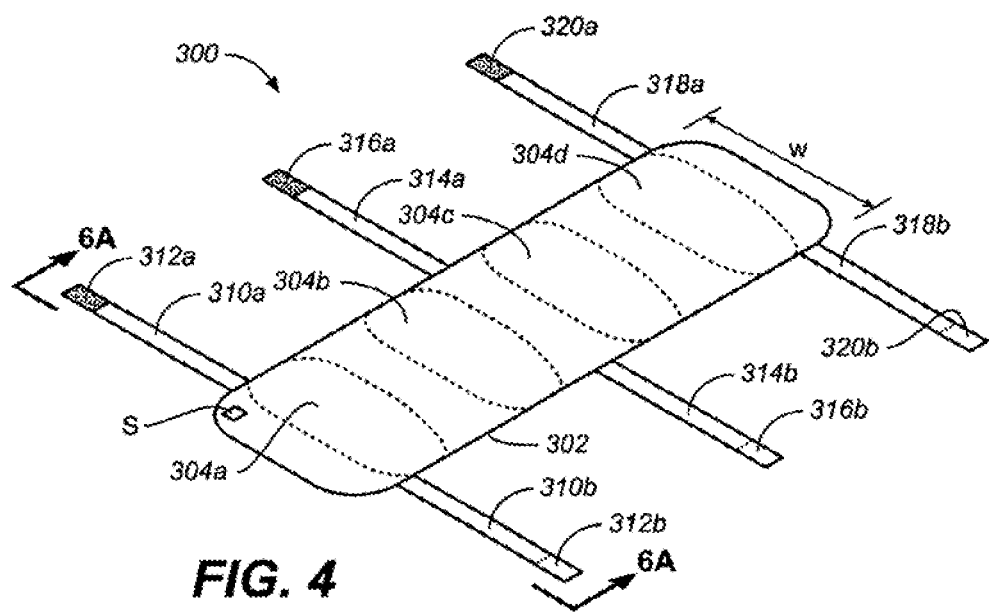
FIG. 4 is a perspective view of another embodiment of vein dilation apparatus according to the invention.
Figure 5:
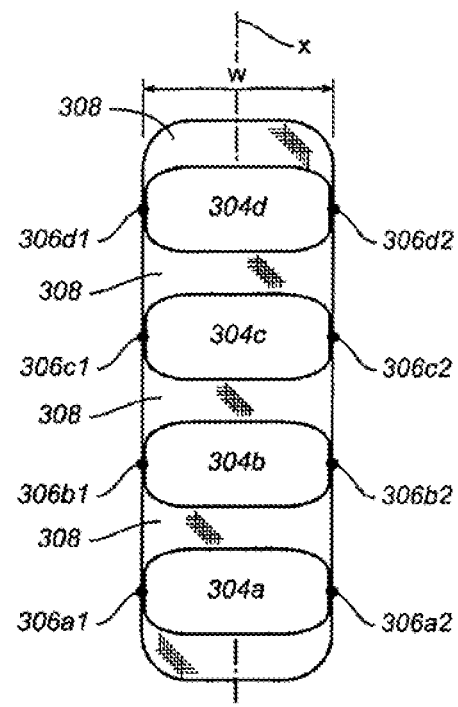
FIG. 5 is a bottom plan view of the vein dilation apparatus of FIG. 4.

Referring to FIGS. 4-6, another embodiment is shown and generally designated with reference numeral 300. Dilation apparatus or device 300 includes housing or casing 302 and a compression member comprising a plurality of separate, longitudinally spaced inflatable balloons or cells housed in casing 302 and secured thereto. Although four inflatable cells 304*a,b,c,d* are shown, more or fewer inflatable cells can be used. The casing typically will be a little longer (e.g., about 2 cm longer) than the treatment length of the apparatus, which corresponds to the distance between far ends of compression members 304*a* and 304*d*, and the components therein typically are selected to minimize the height of the device. As shown in the illustrative embodiment, casing 302 can have a straight configuration along its length and the expandable members arranged along a straight line with their outer edges in mating relation and aligned with the inner side walls of casing 302 as shown. The width of casing 302 is slightly larger than width "W" of the inflatable cells, which is the same as the width of compression members 104 and 104'. Typically, casing 302, which is diagrammatically shown in FIGS. 4 and 5, will have a width of 3-6 cm. This configuration provides a construction that can be readily aligned with a target vein to focus pressure on the target zone or vein as compared to larger devices including devices comprising cylindrical inflation members. The low profile of the casing enhances the ability for one to wear the device for longer periods of time and/or to wear the device while being active. In one embodiment, casing 302 is a hard, rigid material, which can be plastic. The rigid aspect provides various advantages including a mechanism to protect the treated area, which may have become bruised during hemodialysis.

Figure 6A:
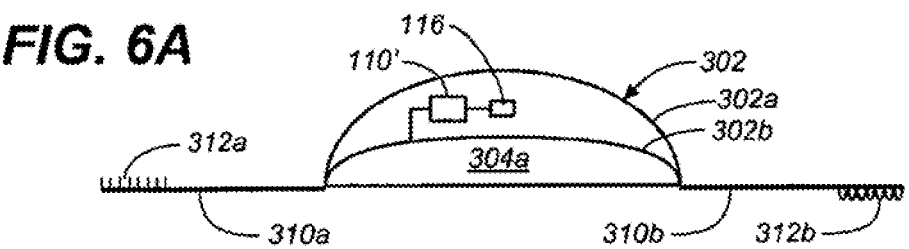
FIG. 6A is an end view of the apparatus of FIG. 5 with one of its inflatable members shown in an uninflated state.
Figure 6B:
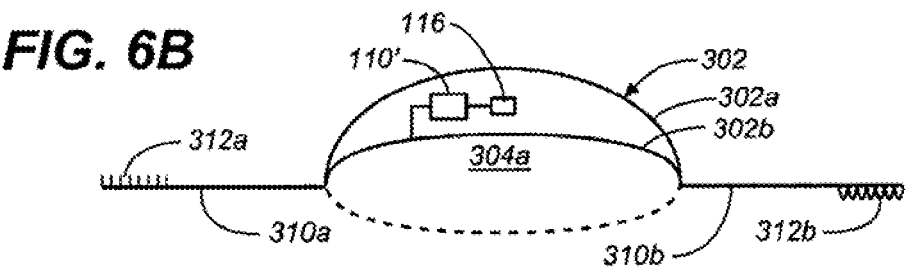
FIG. 6B is an end view of the apparatus of FIG. 5 with one of its inflatable members shown in an inflated state.

Straps 310*a,b*, 314*a,b*, and 318*a,b* extend from casing 302 and include cooperating pairs of fastening mechanisms 312*a* and 312*b*, 316*a* and 316*b*, and 320*a* and 320*b*, which can be hook and loop fasteners or any other suitable fastening mechanism. FIGS. 6A and 6B show a side view of the engaging portions 312*a* and 312*b*.

Referring to FIG. 5, which shows a bottom plan view of dilation apparatus 300, the inflatable cells can be symmetrically aligned along the longitudinal axis "X" of casing 302. A waterproof layer of material 308, such as latex, also can be provided between the inflatable cells. Alternatively, the layer of waterproof material can be provided over the entire bottom surface of casing 302 (including the inflatable cells) so as to provide a waterproof surface over the entire area that contacts the patient's limb. In one variation, heating elements can be provided as described above in connection with the embodiment of FIG. 1. In another variation, the heating elements can comprises a plurality of heating node pairs 306*a*1 and 306*a*2, 306*b*1 and 306*b*2, 306*c*1 and 306*c*2, and 306*d*1 and 306*d*2, which are positioned on opposite sides of each inflatable cell and coupled to a power source through a control unit such as control unit 110' and power source 116.

Referring to FIGS. 6A and 6B, casing 302 can comprise an outer wall 302*a* and inner wall 302*b* to which the inflatable cells or balloons are secured or mounted. The space between walls 302*a* and 302*b* provides a chamber in which power source 116, control unit 110' (including a miniature pneumatic pump), and conduits connecting the inflatable cells to the pneumatic pump in a manner similar to that described in connection with the embodiment illustrated in FIG. 3 can be placed to control the inflation sequence of inflatable cells 304*a,b,c,d* as described above. Power source 116 can be any suitable power source as described above and can be a battery housed in casing 302 as shown. The battery can be a rechargeable or non-rechargeable DC battery and the pump a DC pump. An on-off switch "S" (FIG. 4) can be provided on the outer surface of apparatus 300 to disconnect the power source from the control unit and pressure source (e.g., the pump) or otherwise start or stop the apparatus. Alternatively, either or both the control unit and power source can be mounted on the outer surface of casing 302 or remote therefrom. Solenoid valves can be operatively coupled to the cells and control unit to control fluid flow as described above. FIG. 6A shows cell 304*a* in an uninflated or unexpanded state and FIG. 6B shows cell 304*a* in an inflated or expanded state.

Figure 7:
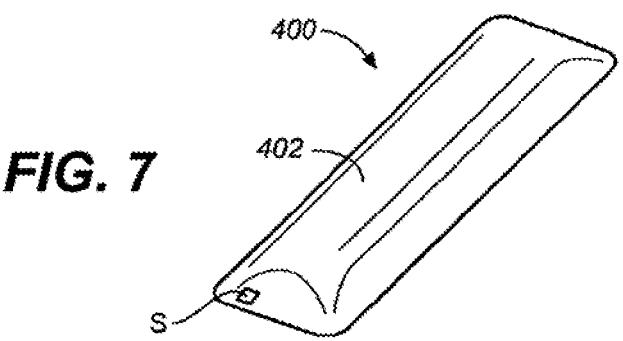
FIG. 7 illustrates another embodiment of vein dilation apparatus according to the invention.
Figure 8:
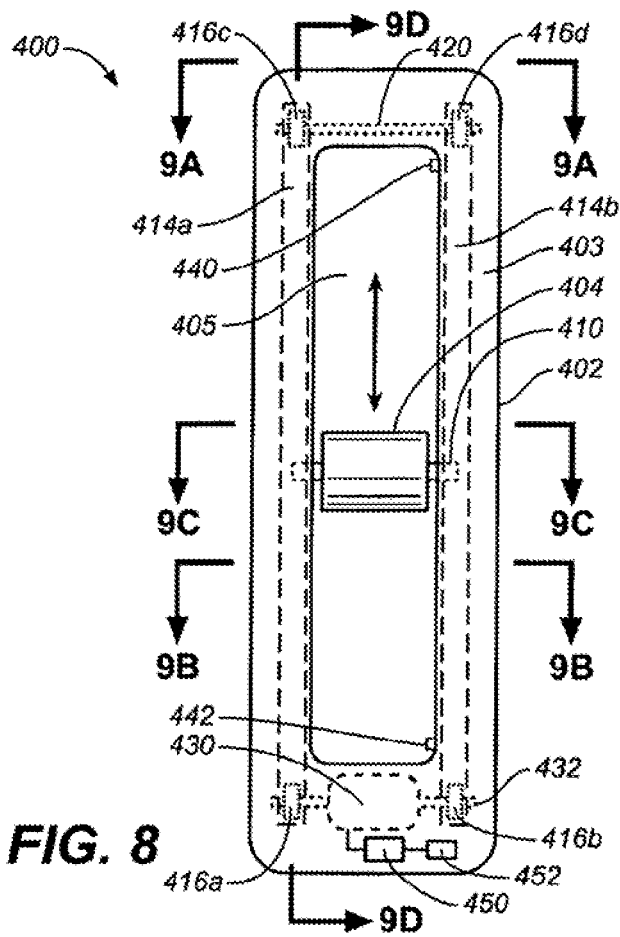
FIG. 8 is a bottom view of the apparatus of FIG. 7.

According to another embodiment of the invention, a compression member is moved along a surface of the patient's limb to apply focused pressure to the target vein. One example of this embodiment is shown in FIGS. 7-9, where exemplary dilation apparatus or device 400 includes a compression member that is driven in one direction and then in a return direction over the target vein. Although various compression member configurations can be used, a roller compression member configuration is shown in the illustrative example. Roller compression member 404 can have a cylindrical shape as shown or any other suitable shape for applying the desired pressure to the patient's limb. For example, compression member 404 can be spherical and form a roller ball that provides more focused pressure than the cylindrical configuration. The spherical roller ball compression member can incorporate the same drive as the cylindrical compression member, which will be described in more detail below, so that it can be moved back and forth along a straight track or path. For example, the spherical roller ball can have an axle that extends through its center like axle 410 described below to accommodate the belt drive illustrated in FIG. 8 or other reciprocating drive mechanism. Further, it should be understood that although a straight track or path is shown, the track or path in any of the embodiments described herein can be configured to form a path corresponding to the path of the target vein if the target vein would otherwise be outside the path of compression member 404.

Returning to FIG. 8, dilation apparatus 400 includes casing 402, which is a rigid casing made from plastic or other suitable material, and which supports compression member 404. Casing 402, which forms a recess in which compression member 404 and the drive reside, can include straps to secure it to the patient's limb and can include straps identical to and arranged like the fastening straps shown in FIG. 4 in connection with dilation apparatus 300. In one embodiment, casing 402 has a width "CW" (FIG. 9A) of 3-6 cm, a height of 2-3 cm, and a length which provides sufficient space for the compression member and which can correspond to the length of casing 302. Referring to the bottom plan view of casing 402, casing 402 has a bottom surface 403 through which is formed a slot 405 that provides access to interior chamber 406 of casing 402. In the illustrative embodiment, compression member 404 is coupled to housing 402 to travel back and forth along slot 405.

Any conventional drive system can be used to repeatedly move the roller member in a forward and return direction. A belt driven roller drive is shown in the illustrative example of FIGS. 8 and 9A-D. Referring to FIG. 8, roller member 404 has an axle 410 having end portions rotatably mounted in brackets 412a,b, which have openings adapted to receive the end portions of axle 410 and are secured to continuous belts 414a,b. Belts 414a,b can be mounted on cylindrical members or hubs 416a,b,c,d. Members 416a,b are secured to the end portions of axle 432 of motor 430, which is secured to casing 402. Members 416c,d are secured to axle 420, which is rotatably mounted to casing 402. Alternatively, axle 420 can be fixedly secured to casing 402 and members 416c,d rotatably mounted on axle 420. As diagrammatically indicated with the arrow in FIG. 9D, when motor 430, which is secured in casing 402, rotates in one direction, it rotates the belts in that direction and moves compression member 404 along slot 405. And when motor 430 rotates in the opposite direction, it rotates the belts in the opposite direction and moves compression member 404 in the opposite direction along slot 405. Any other suitable arrangement for support belts 414a,b can be used as well. For example, hubs 416a-d can be eliminated and the belts directly coupled to motor axle 432 and axle 420.

Figure 9A:
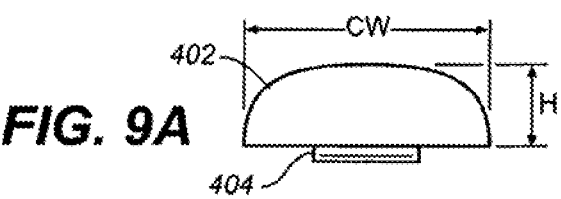
FIG. 9A is an end view of the apparatus of FIG. 8 taken along line 9A-9A.
Figure 9B:
FIG. 9B is a sectional view of the apparatus of FIG. 8 taken along line 9B-9B.
Figure 9C:
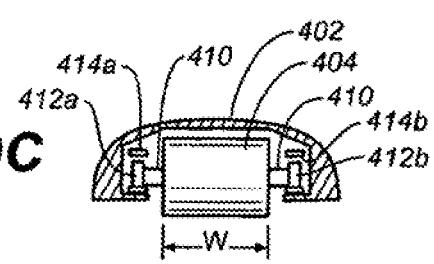
FIG. 9C is a sectional view of the apparatus of FIG. 8 taken along line 9C-9C.
Figure 9D:
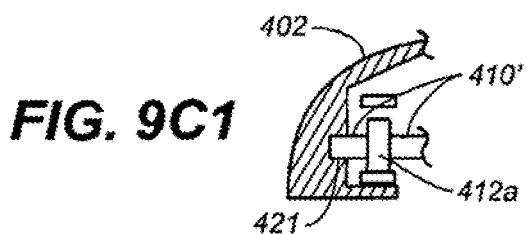
FIG. 9D is a longitudinal sectional view of the apparatus of FIG. 8.
Figure 9D:
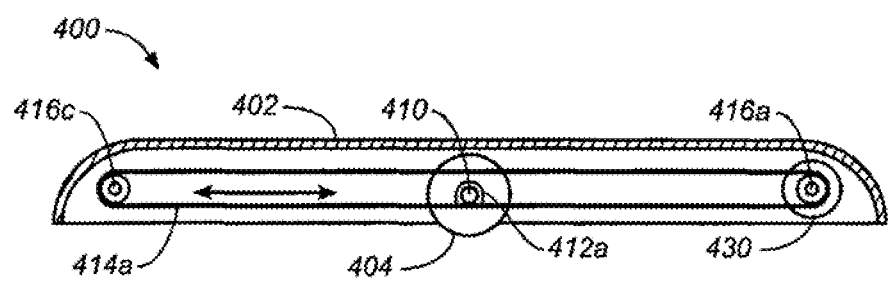

In the variation shown in FIG. 9C1, roller axle 410 is replaced with extended roller axle 410' with each end portion of axle 410' extending into a channel, which is formed in housing 402 and extends the length of slot 403, to limit vertical movement of the roller. Each channel forms a track for compression member 404, which allows the compression member to move along the entire treatment length of the apparatus and, thus, the track or compression member path can have a length equal to the treatment length of the apparatus, which will be described in more detail below. In FIG. 9C1, one channel is designated with reference numeral 421. A similar channel (not shown) is provided on the other side of the slot to receive the other end portion of axle 410'. The axle and channel surfaces can be formed of any suitable material to minimize friction therebetween and can be coated or covered with any suitable material as well.

A description of one conventional control is described hereafter for purposes of example. Drive motor 430 may be a DC motor that is coupled to a rechargeable battery 452 via controller or control unit 450. The direction of rotation of the motor and, thus, the direction of movement of the roller along the slot 405, may be controlled by the control unit 450 which controls the polarity of the voltage applied to the motor. Control unit 450 may be coupled to position sensors 440 and 442 (one at each the end of slot 405) to reverse the motor direction when the roller reaches a position sensor. Position sensors 440 and 442 typically are spaced apart a distance that allows the compression member to move along the entire treatment length of the apparatus and, thus, that spacing can be equal to the treatment length. The position sensors can be magnetic or optical sensors or mechanical limit switches. For example, position sensors 440 and 442 can be limit switches, which are engaged by the roller member when the roller member reaches an end of the track (the track being the portion of slot 405 bounded by the position sensors), and which cause the control unit to reverse the polarity of the battery voltage to the motor.

When the motor axle 432 turns in one direction it drives belts 414a,b, which drive the rotatably mounted roller member in one direction. When the roller member reaches the end of the track, it activates a switch, which causes control unit 450 to reverse the motor direction. This causes the roller member to return or move in the opposite direction along the path. When the roller member reaches the other switch, the same sequence occurs and the motor reverses direction and moves the belt and roller member in the other direction. In this manner, intermittent pressure is applied to a plurality of sections of the vein or an infinite number of points on the vein as the roller member moves along its path. Apparatus 400 typically is secured to the patient's limb in a manner in which compression member 404 provides sufficient pressure to the limb to occlude a portion or point of the target vein that is beneath the compression member.

The following describes an exemplary general procedure for creating a fistula in a patient who has end stage renal disease (ESRD) and has elected hemodialysis as a treatment option and then describes an illustrative example of vein dilation using any of the vein dilation apparatus described above to prepare the vein downstream from the fistula for hemodialysis, which example is provided solely for purposes of example and not to limit the invention.

After a patient has elected hemodialysis as the treatment option, the patient's arm veins are evaluated clinically and measured with ultrasound to find out if there is a vein 3 mm or larger. A 3 mm vein is a suitable candidate for surgical connection to an artery.

The patient is brought to the operating room where the surgeon palpates the patient's arm arteries for a pulse to find a target artery to which the selected vein is to be connected. The surgeon then creates a connection between the selected artery and target vein, thereby forming a fistula. In the treatment example illustrated in FIG. 10, the patient's left radial artery was connected to the patient's left cephalic vein in the region of the patient's wrist. The cephalic and basilic veins, which are the only major veins in a human's arm and which are the only suitable veins in a human's arm for hemodialysis, are shown in dashed line and designated with reference characters "CV" and "BV." The lower portion of the cephalic vein is in the forearm and the upper portion of the cephalic vein is in the upper arm above the elbow.

After the surgery has been completed and the fistula created, dressing is provided over the wound and apparatus constructed according to the principles of the invention (e.g., apparatus 100 (or modified 100 with a multi-cell compression member as shown in FIG. 3), 300, 400, or 400' (described below)) is secured to the patient's limb before the patient leaves the operating room. The apparatus is placed on a patient's forearm (if the fistula were formed at the patient's wrist) or upper arm (if the fistula were formed at the elbow). In either case, the apparatus is arranged so that the compression member is placed downstream from the fistula and over the target vein (vein of interest) to focus pressure provided thereby toward the target vein. The only other veins which will be affected by the treatment are accessory branches coming off the main vein and these are not used for dialysis. In other words, the compression member is placed over the vein proximal to the connection between the target vein and artery, which is referred to as the fistula. The compression member, however, should be arranged so as not to cover the fistula or suture used to close the wound created to provide access to the vein and artery to make the fistula.

Figure 10:
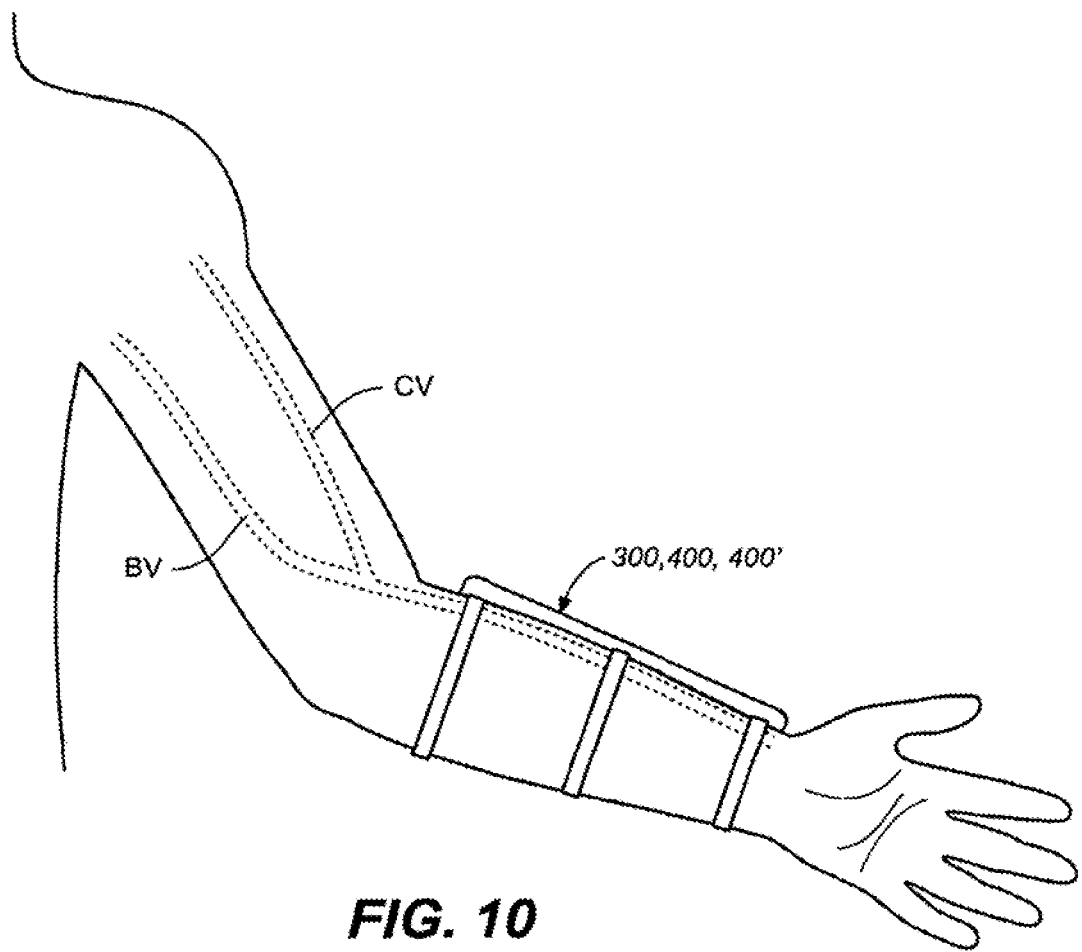
FIG. 10 illustrates use of vein dilation apparatus described herein to dilate a vein in the forearm of a patient.

In the illustrative example, the fistula was created at the patient's left wrist and the apparatus secured to the patient's forearm in a manner to allow intermittent pressure to be applied to the target vein (cephalic vein "CV"), which is to be accessed for hemodialysis, in a manner in which the pressure can be focused on the target vein, with the compression member. As shown in this example, the compression member is configured and arranged to either extend or move in a substantially straight direction along an axial direction or length of the patient's limb without encircling the patient's limb and to exert pressure on a narrow, substantially straight external surface portion of the patient's limb so as to dilate the target vein (e.g., the cephalic vein) thereunder. The compression member extends or runs substantially parallel to the cephalic vein as shown in FIG. 10. As described above, the compression member typically will have a width from 1 cm to and including 2 cm and more typically a width of 1.5 cm.

The compression member applies occlusive pressure on the patient's limb, which is then transmitted to the target vein to temporarily occlude the target vein. In the case where apparatus 100 is used, a substantially uniform pressure is applied intermittently to the target vein. For example, compression member 104 is inflated to a pressure, which is sufficient to occlude the target vein, for about five seconds and then allowed to deflate for about three seconds and this cycle repeated for the treatment period. When the multi-cell apparatus of FIG. 3 or FIG. 4 or roller apparatus 400 is used, the pressure profile can correspond to a wave. In one method, apparatus 300 is configured to pressurize each cell independently so that a pressure wave moves, for example, from the wrist toward the elbow. In one example where the three cell embodiment shown in FIG. 3 is used, the cell closest to the wrist is inflated to a pressure, which is sufficient to occlude the target vein, for about five seconds and allowed to deflate while the middle cell adjacent thereto is inflated to a pressure, which is sufficient to occlude the target vein, for the same period of time, and then the next cell adjacent to the elbow is inflated to a pressure, which is sufficient to occlude the target vein, for the same period of time while the middle cell is allowed to deflate. This cycle is repeated for the treatment period, which corresponds to the period of time in which the apparatus operates continuously on the patient's limb. In a method using apparatus 400, the apparatus is set to move the compression member back and forth over the target vein at a speed of about one cm/sec for the treatment period. The rolling compression member provides a stroking pressure wave to the vein as it moves over it. In this manner, intermittent occlusive pressure is applied to a plurality of sections of or an infinite number of points on the target vein.

The overall treatment and the frequency of the treatment periods used to provide the desired vessel dilation can vary from patient to patient. Treatment periods typically will range from about one to about eight hours and typically will be provided daily up to about eight weeks. The vein dilation can be periodically checked to determine if treatment be continued. The device configuration including its low and narrow profile and its ability to cover the target vein make it especially suitable for relatively long periods of use, while allowing the patient to be relatively active.

The dilation method can include application of heat to the patient's limb with the apparatus as described above. Typically, the heating element(s) will maintain the temperature of the portion of the apparatus in contact with the patient's skin to about 98 to 150 degrees Fahrenheit. In one example, the control unit is set to provide a constant temperature of 120 degrees Fahrenheit. at the surface of the apparatus that contacts the patient's limb.

In a further method, a topical vasodilating agent such as nitric oxide is applied to the patient's skin over the target vein prior to each use of the vein dilation apparatus.

Pressure alone, pressure in combination with heat or the topical dilation agent, or pressure, heat and the topical agent can be used throughout the treatment period.

According to another embodiment of the invention, dilation apparatus constructed according to the principles of the invention is used between hemodialysis sessions, which typically are scheduled three times per week. The apparatus would be worn and pressure applied for up to about an eight hour period during the days when hemodialysis is not scheduled. Such ongoing vein stimulation can help insure vein dilation continues for a longer period of time and provide longer patency of the fistula.

According to another method of the invention, dilation apparatus constructed according to the principles of the present invention is used before the fistula is made. In this method, the apparatus typically will be used daily for about one month before the surgery to dilate the target vein to a desired diameter for the fistula. The pressure and daily treatment periods will be as described above regarding post surgery treatment. The foregoing treatment is carried out to prepare and dilate the vein prior to surgical connection. However, this treatment also can be done to assist in vein dilation proximal to an area where an arterio-venous graft has been constructed to provide dialysis. In this example, the apparatus typically will be applied to the upper arm cephalic vein and the process performed before graft failure.

According to another method of the invention, dilation apparatus constructed according to the principles of the present invention, is applied at a new site to dilate another vein while hemodialysis using the previously dilated vein continues. For example, apparatus being used between hemodialysis sessions can be moved from the left arm cephalic vein to the right arm cephalic vein when the physician concludes that the left arm cephalic vein is nearing failure. Indications of such failure can include, but are not limited to, significantly reduced blood flow from the fistula. In this manner, the patient can commence dilating another vein in preparation for surgical creation of another fistula. This can improve the efficiency of the overall hemodialysis treatment.

Figure 11A:
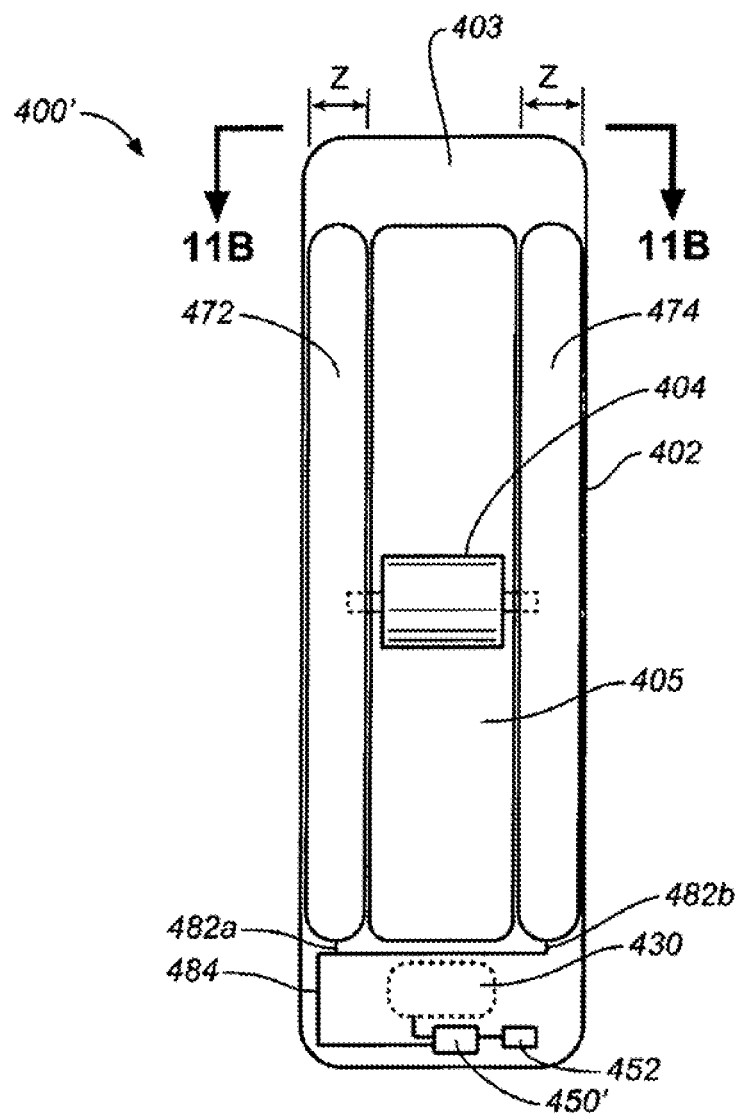
FIG. 11A a bottom view of a variation of the embodiment of FIGS. 7 and 8.
Figure 11B:
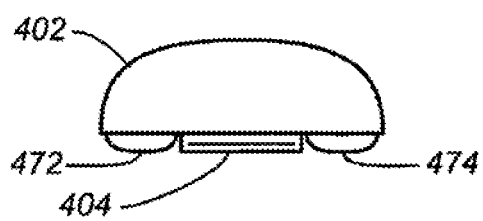
FIG. 11B is an end view of the apparatus of FIG. 11A taken along line 11B-11B.

Referring to FIGS. 11A and 11B, another embodiment of the invention is shown and generally designated with reference numeral 400'. Dilation apparatus or device 400' is the same as apparatus 400 with the exception that apparatus 400' further includes inflatable or expandable compression members or balloons 472 and 474 (which are secured to the bottom surface 403 of housing 402 and extend in a longitudinal direction of housing 402 on opposite sides of slot 405) and their accompanying fluid delivery conduits, and the control unit of apparatus 400 modified to include a pressure source and timing circuit to maintain balloons 472 and 474 inflated throughout the treatment period to partially occlude the branch vessels, which branch from the target vein, while roller compression member 404 moves back and forth over the target vein to transmit a stroking pressure wave thereto to dilate the target vein as described above. In this manner, dilation of the branch vessels, which branch from the target vein, is reduced or minimized during treatment. Balloons 472 and 474 also prevent the branch vessels from carrying blood away from the target vein or they reduce the amount of blood flow that they carry away from the target vein, thus assisting with enlargement of the target vein. The control unit is designated with reference numeral 450' and is coupled to power source 452 in the same manner as control unit 450 is coupled to power source 452 in apparatus 400. Conduits 482*a,b* are fluidly coupled to manifold 484, which is fluidly coupled to the pressure source in control unit 450', which controls pressure delivery from the pressure source to compression members or balloons 472 and 474. Balloons 472 and 474 may be inflated to provide continuous occlusive pressure to the branch vessel during a treatment period. However, it should be understood that balloons 472 and 474 need not be continuously inflated during a treatment period. Solenoid valves or any suitable means as described above can be used to inflate and/or deflate balloons 472 and 474 according to a desired inflation-deflation profile. The length of balloons or compression members 472 and 474 typically is the same as the length of the track in which or path along which roller compression member 404 moves (i.e., the distance which the roller compression member travels in each direction) and typically will be at least 5 cm as described in more detail below. Further, expandable members or balloons similar to balloons 472 and 474 can be combined with any other embodiment described herein and positioned in a similar manner.

During hemodialysis, two needles typically are used. One needle is used to draw blood, while the other provides a return for filtered blood. The needles typically are spaced apart at least 5 cm and therefore at least 5 cm of dilated vessel may be required. The devices described herein have a treatment length, which corresponds to the length of the expandable member 104 or 104', the distance between the outermost margins of cells 304*a* and 304*d*, or the length of the path or track in which the moving (e.g., reciprocating) compression device moves and typically will be at least 5 cm, and more typically the treatment length will be 5-25 cm depending on the size of the patient's limb (e.g., the patient's upper arm or lower arm), and even more typically it will be 20-25 cm. The length of the apparatus housings or casings (e.g., housing or casing 302 or 402), typically will be about 2 cm longer than the apparatus treatment length. The housing or casing length typically will be less than or equal to 40 cm so as not to overlap a patient's joint (e.g., the elbow joint), and more typically will be less than or equal to 30 cm. This apparatus or any of dilation apparatus 100 or modified apparatus 100 with a multi-cell compression member as shown in FIG. 3 and described above, 300, and 400 are constructed to provide long term vein dilation sufficient for hemodialysis or maintenance of vein dilation during hemodialysis treatment.

In another form of the invention, a method of utilizing the previously described compression device includes a modification to the protocol previously described and described in more detail hereinafter. The new protocol was tested and the results of such test is included herein.

The compression device is a previously described, self-contained, miniaturized, wearable intermittent pneumatic compression device. The small control unit is integrally attached to an inflatable cuff that is held to the upper extremity using a hook and loop attachment. Patients are able to apply and remove the device themselves using only the contralateral hand. The compression device is battery operated and has a single control to turn it on or off. All pressure and timing parameters are preset at the factory: The bladder is inflated to a pressure of 60 mmHg and held for 20 seconds then deflated to 10 mmHg pressure for 55 seconds before the next inflation cycle.

The study also included a control in the form of sham units which look the same and have the same timing as therapeutic devices but inflate to 10 mmHg and deflate to zero pressure.

The study utilized a dedicated research coordinator to conduct the trial. Eligible patients had early stage 5 renal failure and were referred to the vascular access surgeons for fistula placement. Patients were educated about fistula placement surgery and the active research trial in the center of the study. Patients were enrolled in the trial after full education and were placed randomly into either the control or treatment group by the research coordinator. Patients started wearing either device after surgical success was documented within one week of surgery (recovery time period) by either a palpable thrill or documented flow in the vein with duplex. The demographics of each patient were recorded: age, sex, cause of renal failure, baseline blood pressure, present medications, previous access history, catheter placement date, and fistula surgery date.

Vein diameter was measured either intra-operatively or by preoperative duplex exam per protocol and using standard vascular lab protocols for vein imaging. Measurements were made pre- and post-surgery by duplex (DOPPLER—Mindary Model—M7 with PROBE: Ultrasonic Transducer Linear Probe8-12 MHz) without a tourniquet, taking the largest diameter reading. Time to measure and room climate were standardized in order to avoid spasms. All measurements were evaluated for accuracy and recorded. All patients wore the compression device after fistula creation and clinical assessment by surgeon. For the study, surgical fistula were created per standard surgical protocols to connect the inflow artery and outflow vein either at the wrist or antecubital location. Reflective of global fistula preferences amongst surgeons, only forearm RCF or upper arm BCF were created. Using standard vascular surgical practices of careful vein and artery dissection, vein mobilization, and anastomosis creation, successful fistulas were created for each patient. Patients were instructed to wear the device for a total of 6 hours daily, on an intermittent basis, for a 30-day period. Patients and their families recorded usage times in a daily log.

The study inclusion criteria included the following: end stage renal disease (ESRD) patients presently undergoing dialysis with a catheter, future hemodialysis patient planning to have an upper arm or forearm AVF placed, willing to comply with compression device application, understanding where, how and when to apply the compression device.

The study exclusion criteria included the following: poor understanding of trial, arm infection, fistula thrombosis, restless arms, synthetic grafts, systolic blood pressure below 70 mmHg during hemodialysis, mild pain intolerance, or skin disorders requiring frequent medical attention.

Figure 13:
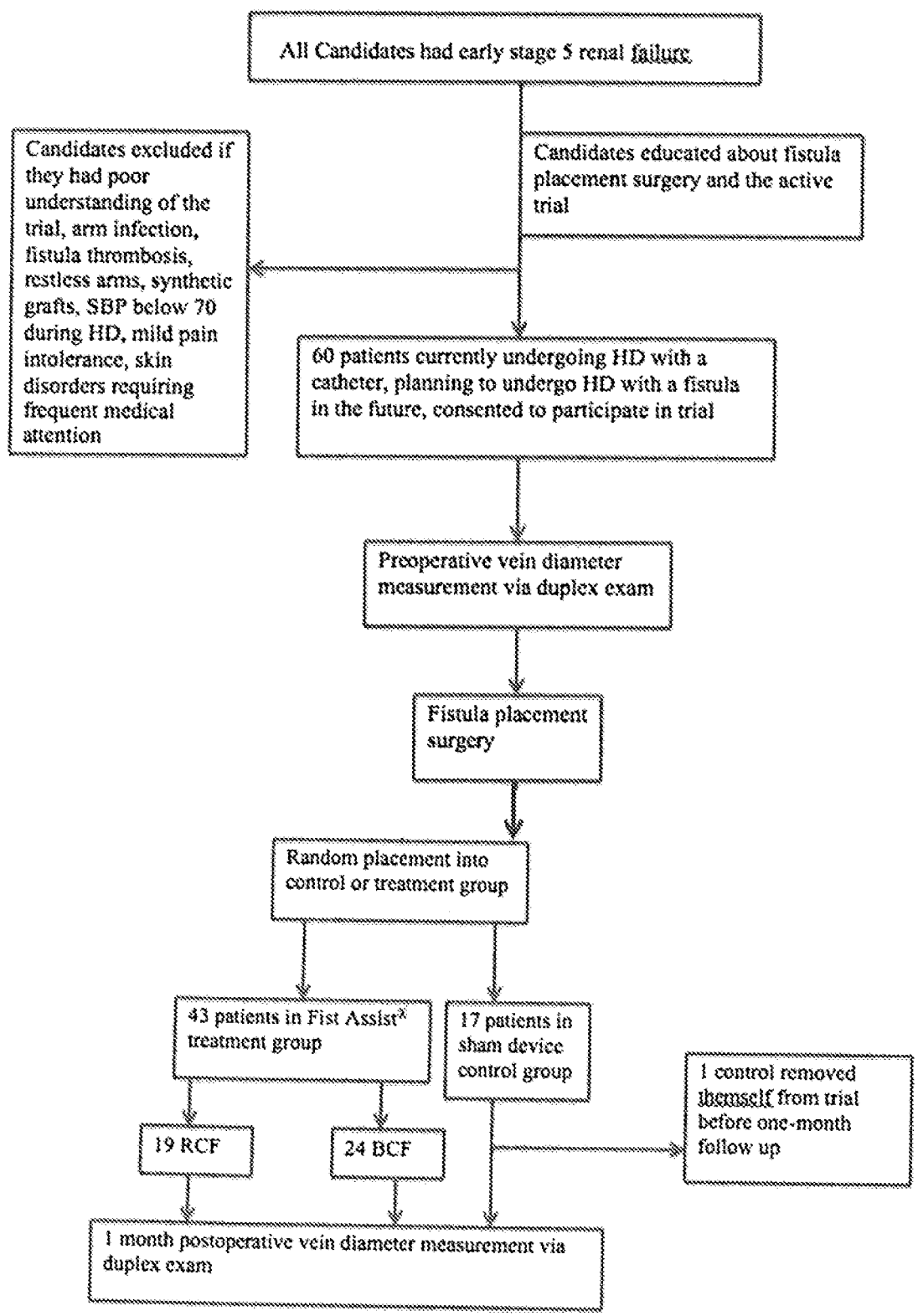
FIG. 13 is a flowchart showing patient selection criteria.

After thirty days, patients had duplex exam measurements done. All complications, untoward events, thrombosis and other issues were recorded. Patient selection criteria and research protocol are further detailed in FIG. 13.

The patient demographics included a total of 43 patients in the treatment group. The total group included 19 patients with RCF and 24 with BCF at the one-month follow up. There were a total of 16 patients in the control group, including 2 patients with RCF and 14 with BCF. Only one patient from the treatment group and the control group removed themselves from the trial before the one-month follow up. Patient risk factors were similar to the global renal failure epidemic with diabetes and hypertension being very common in the enrolled patients. FIG. 12 shows the patient demographics (in %) for both treatment and control groups combined by gender, presence of diabetes mellitus (DM), presence of hypertension (HTN), and age. For age, the mean and standard deviation are shown by gender. As can be observed, a significant number of the patients (89.83%) had hypertension. These patient demographics are typical for renal failure patients globally including the US Renal failure prevalence and reflect the standard risk factors for renal failure.

Figures 14, 15:
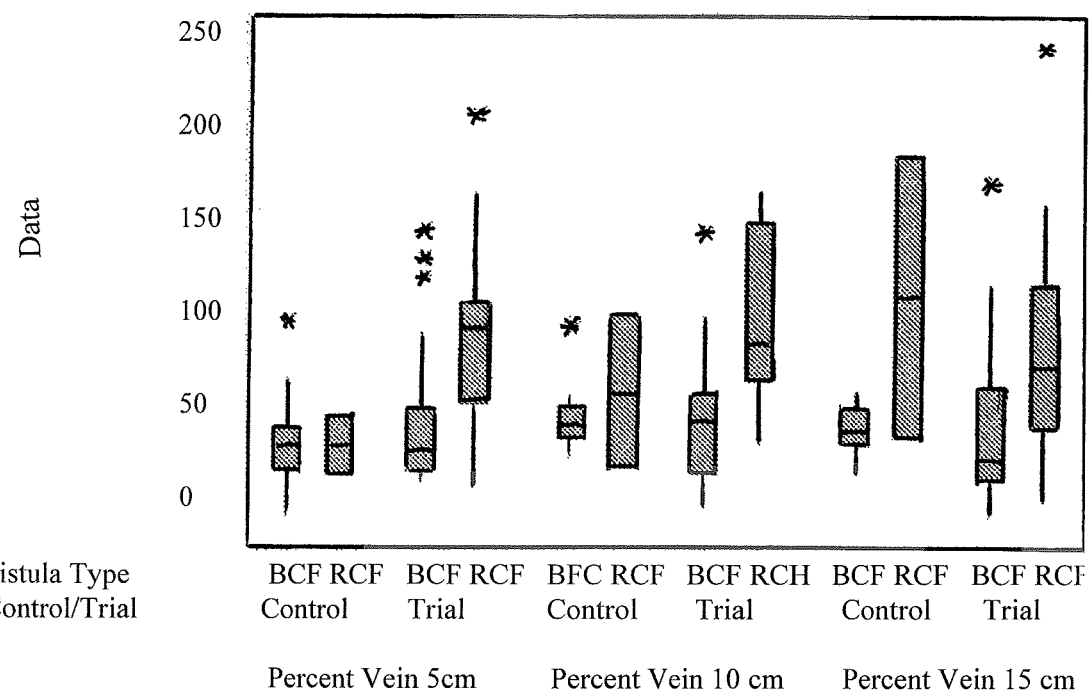
FIG. 14 is a table showing percent increase results in the case study of FIG. 12.
FIG. 15 is a box plot of one month data on percentage increase in vein size diameter for the case study of FIG. 12.

Results of the study show a percentage increase in vein dilation after one month for the RCF and BCF treatment groups at proximal distances of 5 cm, 10 cm, and 15 cm from the anastomosis, respectively in FIG. 14; shows the mean, standard deviation, and standard error (SE) of the mean, based on the sample sizes shown. Additionally, the first quartile (Q1), the median, and the third quartile (Q3) values are also shown in the table. These values, therefore, convey a measure of the average increase in vein size dilation as well as the variability in this statistic. It is important to note that mean increases in vein size dilation for the trial group with RCF outperform that for those with BCF at all three proximal locations. Statistical tests for such comparisons are discussed subsequently. A graphical display of these results is further depicted in FIG. 15, which shows a box plot of percent vein increases for RCF and BCF control and trial groups at all three proximal locations. The box plot shows measures of location and variability of the percentage increase in vein dilation, by control and treatment group, and by fistula type within each group. The median value is indicated by a line inside the box, with the first and third quartiles representing the lower and upper edges of the box. Outliers, shown by an * in the plot, are values that are more that one and a half times the inter-quartile range, from either edge of the box. All of the outliers are on the high side.

FIG. 16 compares the percentage increase in vein dilation of those in the RCF treatment group (CLASS=1), the control group of all patients (CLASS=2), and the treatment group BCF only (CLASS=3). As in FIG. 14, the mean, standard deviation, standard error of the mean, first quartile, median, and the third quartile values are shown for each CLASS and for each proximal location. At all proximal distances, percentage vein increase for those with an RCF outperforms that of the controls. Statistical tests for such comparisons are subsequently discussed.

Hypothesis tests on the mean percentage increase in vein size dilation are conducted for the RCF and BCF treatment groups. A one-sided, two-sample t-test is performed to determine if the mean percentage increase in vein size dilation after one month for the RCF treatment group significantly exceeds that for the BCF treatment group. At proximal distances of 5 cm, 10 cm, and 15 cm, the results are significant (t=3.50, p-value=0.001; t=4.32, p=0.000; t=2.92, p-value=0.003, respectively).

A one-sided, two-sample t-test is also performed to determine if the mean percentage increase in vein size dilation for the RCF treatment group exceeds that for the control group (BCF and RCF controls combined) at one month. The results are significant at proximal distances of 5 cm, 10 cm, and 15 cm (t=4.69, p-value=0.000; t=4.26, p-value=0.000; t=2.23, p-value=0.016, respectively).

It is well known that AVF creation followed by dilation and maturation is important to ensure hemodialysis for renal failure patients. Yet, because of their low maturation rates and associated complications, only 14% of US patients start hemodialysis with an AVF, and AVF use continues to be low throughout the world. RCF are considered first choice, when creating an AVF, because their lower flow rates lead to lower risks of complications. BCF are exposed to higher flow volumes, which are associated with risks such as arm swelling, steal syndrome, pseudo aneurysm, and cephalic arch stenosis. However, the lower flow volume rate associated with RCF makes it difficult to mature this type of fistula. Efficient fistula maturation is extremely important so that patients may begin dialysis with a functioning fistula. The primary patency of fistulas was found to be inferior among patients starting hemodialysis with a catheter, as compared to those starting hemodialysis with a mature fistula.

In the present study, the effect of a novel intermittent pneumatic compression device, compression device, on percent vein dilation after AVF placement was studied, with a particular interest in RCF. With the intermittent pneumatic compression device placed proximal to the anastomosis and directly on the outflow vein may be the first device of its type to help patients with early fistula enlargement. This study demonstrates the early benefit of pneumatic compression on RCF vein dilation as early as one month after fistula placement surgery commencing after a recovery period of approximately one week.

Application of the compression device was very simple and well tolerated by patients. The compression device was found to be safe and of no significant risk or danger to the patient population, which had the usual systemic risk factors for universal renal failure and surgical complications after surgery and compression device. Initial concerns were directed at the device's potential to cause vein and arterial thrombosis, increased pain, skin reactions, or bleeding from the site. However, zero patients who used the compression device experienced adverse complications or thrombosis of their AVF, and the device held up to its non-significant risk indications. The device, which had a maximum inflation pressure of 60 mm Hg, based on the well-studied hemodynamics of acute arteriovenous fistulas, posed no risk for arterial occlusion since patients were excluded if they had a systolic blood pressure less than 70 mm Hg. The initial pilot studies demonstrated the device was not harmful to patients, their fistulas or their overall health.

Review of the data endpoints demonstrates that the compression device leads to significant vein dilation in patients with RCF after one month (30 days), as compared to patients in the treatment group with BCF. Additionally, a significant increase in mean vein dilation was demonstrated in the RCF treatment group at all proximal distances, as compared to controls, for BCF and RCF patients combined, at one month. The study demonstrated that an average increase in vein diameter of 60% was associated with successful fistula maturation. It is important to note that, after 1 month, the mean increase in vein diameter for patients in the treatment group with RCF was greater than 60% at proximal distances of 5 cm, 10 cm, and 15 cm (see FIG. 14). Furthermore, after 1 month, the mean increase in vein diameter for patients in the treatment group with BCF were all lower than 60%. This data demonstrates that the compression device may preferentially assist maturation of RCF. Furthermore, the device's potential is promising because many patients found it comfortable to wear and better tolerated than squeezing a ball, wearing rubber band occlusion devices, or waiting for fistulas to mature on their own.

All surgeons in the study followed the standard practices of fistula creation and surgical steps. RCF and BCF creation was done per standard accepted surgical techniques as developed and followed by vascular access surgeons.

This data demonstrates that the compression device has the potential to help clinical RCF development. An easy to wear and well tolerated external device that can help RCF maturation and dilation is a very important finding. If this can translate to earlier dialysis starts and less catheter contact time, the device will assist in renal failure care and decrease costs associated with vascular access.

The most recent protocols for fistula surgery follow a method referred to as "the rule of 6s." This protocol calls for a fistula vein length of at least 6 mm, a vein location of at the most 6 mm from the skin exterior, a vein flow rate of at least 600 ml/minute, and a fistula length of at least 6 cm.

Utilizing these parameters, the present invention provides for applying the compression device after fistula surgery has been performed and after a one week recovery period for a minimum of one hour three times per day, and preferably for a minimum of two hours three times per day. This post surgery procedure is done for approximately four to six weeks, after the recover period of one week.

Utilizing these parameters, the present invention provides for applying the compression device before fistula surgery has been performed for a minimum of one hour three times per day, and preferably for a minimum of two hours three times per day. This pre-surgery procedure is done for at least three months prior to surgery and preferably at least six months prior to surgery. The procedure is based upon reaching a target vein diameter prior to surgery of at least 3.5 mm.

Any feature described in any one embodiment described herein can be combined with any other feature or features of any of the other embodiments whether preferred or not.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto.

The invention claimed is:

1. A method for dilating a target vein of a patient being treated for hemodialysis comprises securing a limb compression device to a limb of a patient being treated for hemodialysis post surgical formation of a fistula at a fistula portion of a target vein, the limb being where the target vein resides and with the limb compression device intermittently applying a first effective amount of pressure of 60 mmHg or higher followed by a second effective amount of pressure of no less than 10 mmHg to the target vein downstream of the fistula portion multiple times a day while allowing the patient to be ambulatory and for an effective amount of time to dilate the fistula portion of the target vein to a size suitable to provide access for hemodialysis.

2. The method of claim 1, wherein the limb compression device is actuated for a time period of at least one hour at least three times a day.

3. The method of claim 1, wherein the limb compression device is actuated for a time period of at least two hours at least three times a day.

4. The method of claim 1, wherein the first effective amount of pressure is applied for at least 20 seconds.

5. The method of claim 4, wherein the second effective amount of pressure is applied for at least 55 seconds.

6. The method of claim 1, wherein the device is actuated upon the limb for between four weeks and six weeks after a one week recovery time period.

7. The method of claim 1, wherein in addition to the intermittent pressure being applied to the target vein post surgical formation of a fistula the intermittent pressure is also applied to the target vein prior to surgical formation of the fistula.

8. The method of claim 7, wherein the intermittent pressure applied to the target vein prior to surgical formation of the fistula is conducted for a period of not less than three months prior to surgery.

9. The method of claim 7, wherein the intermittent pressure applied to the target vein prior to surgical formation of the fistula is conducted for a period of not less than six months prior to surgery.

10. A method for dilating a fistula portion of target vein of a patient being treated for hemodialysis comprising the steps of:
(A) determining the size of the fistula portion of the target vein;
(B) applying an intermittent pressure to the target vein downstream of a fistula after the surgical formation of the fistula but prior to hemodialysis, the intermittent pressure being a first constant pressure of at least 60 mmHg followed by a second constant pressure of at least 10 mmHg the intermittent pressure being applied for a treatment period multiple times a day until the fistula portion achieves a diameter size of at least 3.5 mm.

11. The method of claim 10 wherein step (B) the treatment period is not less than two weeks commencing after a recovery time period post surgical formation of the fistula.

12. The method of claim 10 wherein step (B) the treatment period is not less than four weeks commencing after a recovery time period post surgical formation of the fistula.

13. The method of claim 10 further comprising the step of (C) applying an intermittent pressure to the target vein downstream of the fistula prior to the surgical formation of the fistula.

14. The method of claim 13 wherein step (C) the applying of intermittent pressure prior to surgical formation of the fistula commences at least three months prior to formation of the fistula.

15. The method of claim 13 wherein step (C) the applying of intermittent pressure prior to surgical formation of the fistula commences at least six months prior to formation of the fistula.

16. The method of claim 10 wherein said first constant pressure is held for 20 seconds or more, and wherein said second constant pressure is held for 55 seconds or more.

17. A method for dilating a target vein of a patient being treated for hemodialysis comprises securing a limb compression device to a limb of a patient being treated for hemodialysis prior to surgical formation of a fistula, the limb being where the target vein resides and with the limb compression device applying an effective amount of pressure intermittently to the target vein downstream of a fistula portion of a target vein multiple times a day while allowing the patient to be ambulatory and for an effective amount of time to dilate the target vein to a size suitable to provide access for hemodialysis, the effective amount of pressure including a first constant pressure of at least 60 mmHg followed by a second constant pressure of at least 10 mmHg.

18. The method of claim 17, wherein the limb compression device is actuated for a time period of at least one hour at least three times a day.

19. The method of claim 17, wherein the limb compression device is actuated for a time period of at least two hours at least three times a day.

20. The method of claim 17, wherein the first constant pressure is held for at least 20 seconds.

21. The method of claim 20, wherein the second constant pressure is held for at least 55 seconds.

22. The method of claim 17, wherein the device is actuated upon the limb for at least three months prior to fistula formation surgery.

23. The method of claim 17, wherein in addition to the intermittent pressure being applied to the target vein prior to surgical formation of the fistula the intermittent pressure is also applied to the target vein after surgical formation of the fistula.

24. The method of claim 23, wherein the intermittent pressure applied to the target vein after to surgical formation of the fistula is conducted for a period of not less than two weeks.

25. The method of claim 23, wherein the intermittent pressure applied to the target vein prior surgical formation of the fistula is conducted for a period of not less than four weeks.

26. A method for dilating a fistula portion of target vein of a patient being treated for hemodialysis comprising the steps of:
(A) determining the size of a target vein for creating a fistula at a fistula portion in the target vein;
(B) applying an intermittent pressure to the target vein downstream of the fistula site prior to the surgical formation of the fistula but prior to hemodialysis, the intermittent pressure being applied for a treatment period multiple times a day until the target vein achieves a diameter size of at least 3.5 mm, with the treatment period including a first constant pressure of at least 60 mmHg followed by a second constant pressure of at least 10 mmHg.

27. The method of claim 26 wherein step (B) the intermittent pressure treatment period is for a period of not less than three months prior to surgical formation of the fistula.

28. The method of claim 26 wherein step (B) the intermittent pressure treatment period is for a period of not less than six months prior to surgical formation of the fistula.

29. The method of claim 26 further comprising the step of (C) applying an intermittent pressure to the target vein after formation of the fistula.

30. The method of claim 29 wherein step (C) the applying of intermittent pressure after surgical formation of the fistula lasts for a period of at least two weeks.

31. The method of claim 29 wherein step (C) the applying of intermittent pressure after surgical formation of the fistula lasts for a period of at least four weeks.

32. A method for dilating a target vein of a patient being treated for hemodialysis comprises securing a limb compression device to a limb of a patient being treated for hemodialysis both prior to and after surgical formation of a fistula, the limb being where the target vein resides and with the limb compression device applying an effective amount of pressure intermittently for a first pressure of at least 60 mmHg followed by a second pressure of at least 10 mmHg to the target vein downstream of a fistula portion of a target vein multiple times a day while allowing the patient to be ambulatory and for an effective amount of time to dilate the target vein to a size suitable to provide access for hemodialysis.

33. The method of claim 32, wherein the limb compression device is actuated both prior to and after surgical formation of the fistula for a time period of at least one hour at least three times a day.

34. The method of claim 32, wherein the limb compression device is actuated both prior to and after surgical formation of the fistula for a time period of at least two hours at least three times a day.

35. The method of claim 32, wherein the first pressure is held for at least 20 seconds.

36. The method of claim 32, wherein the second pressure is held for at least 55 seconds.

37. The method of claim 32, wherein the device is actuated upon the limb for between four weeks and six weeks after a one week recovery time period post formation of the fistula.

38. The method of claim 32, wherein the intermittent pressure applied to the target vein prior to surgical formation of the fistula is conducted for a period of not less than three months.

39. The method of claim 32, wherein the intermittent pressure applied to the target vein prior to surgical formation of the fistula is conducted for a period of not less than six months.

40. A method for dilating a fistula portion of target vein of a patient being treated for hemodialysis comprising the steps of:
(A) determining the size of a target vein at the site of a surgical formation of a fistula;
(B) applying an intermittent pressure to the target vein downstream of the fistula portion site both before and after the surgical formation of the fistula but prior to hemodialysis, the intermittent pressure being applied to the target vein prior to surgical formation of the fistula portion for a treatment period multiple times a day until the target vein at the fistula site achieves a diameter size of at least 3.5 mm, with the treatment period including a first constant pressure of at least 60 mmHg followed by a second constant pressure of at least 10 mmHg.

41. The method of claim 40 wherein step (B) the treatment period after formation of the fistula is not less than two weeks commencing after a recovery time period post surgical formation of the fistula.

42. The method of claim 40 wherein step (B) the treatment period after formation of the fistula is not less than four weeks commencing after a recovery time period post surgical formation of the fistula.

43. The method of claim 40 wherein step (B) the treatment period before formation of the fistula commences at least three months prior to formation of the fistula.

44. The method of claim 40 wherein step (B) the treatment period before formation of the fistula commences at least six months prior to formation of the fistula.

45. The method of claim 44 wherein step (B) the treatment period after formation of the fistula is not less than two weeks commencing after a recovery time period post surgical formation of the fistula.

* * * * *